(12) United States Patent
Chang et al.

(10) Patent No.: US 8,396,281 B2
(45) Date of Patent: Mar. 12, 2013

(54) APPARATUS AND METHOD FOR INSPECTING SUBSTRATE INTERNAL DEFECTS

(75) Inventors: Jen-Ming Chang, Taoyuan County (TW); Yu-Hsi Lee, Taoyuan County (TW); Yen-Chun Chou, Taoyuan County (TW); Cheng-Kai Chen, Taoyuan County (TW); Jui-Yu Lin, Taoyuan County (TW)

(73) Assignee: Delta Electronics, Inc., Taoyuan County (TW)

( * ) Notice: Subject to any disclaimer, the term of this patent is extended or adjusted under 35 U.S.C. 154(b) by 354 days.

(21) Appl. No.: 12/731,662

(22) Filed: Mar. 25, 2010

(65) Prior Publication Data
US 2011/0135188 A1    Jun. 9, 2011

(30) Foreign Application Priority Data

Dec. 4, 2009  (TW) ................. 98141511 A
Jan. 8, 2010  (TW) ................. 99100393 A (51) Int. Cl.
*G06K 9/00* (2006.01)

(52) U.S. Cl. ............ 382/149; 382/131; 356/237.1; 356/237.6

(58) Field of Classification Search ............ 382/141, 382/149; 356/237.1–237.6
See application file for complete search history.

(56) References Cited

U.S. PATENT DOCUMENTS

| | | | | |
|---|---|---|---|---|
| 5,355,213 A | * | 10/1994 | Dotan | 356/239.7 |
| 5,887,077 A | * | 3/1999 | Bongardt et al. | 382/149 |
| 6,331,889 B1 | * | 12/2001 | Kaupp | 356/239.1 |
| 6,927,848 B2 | * | 8/2005 | Gerstner et al. | 356/239.1 |
| 7,511,807 B2 | * | 3/2009 | Fang et al. | 356/239.7 |
| 8,077,305 B2 | * | 12/2011 | Owen et al. | 356/237.1 |
| 2007/0165213 A1 | * | 7/2007 | Fang et al. | 356/239.1 |

FOREIGN PATENT DOCUMENTS

| | | |
|---|---|---|
| JP | 61284646 A | 12/1986 |
| JP | 8210985 A | 8/1996 |
| JP | 10339705 A | 12/1998 |
| JP | 2001305072 A | 10/2001 |

OTHER PUBLICATIONS

China Official Action issued on Mar. 21, 2012.
Japan Official Action issued on Jun. 5, 2012.

* cited by examiner

*Primary Examiner* — Tarifur Chowdhury
*Assistant Examiner* — Isiaka Akanbi
(74) *Attorney, Agent, or Firm* — Chun-Ming Shih; HDLS IPR Services (57) ABSTRACT

A method for inspecting substrate internal defects is disclosed. The method provides at least one light source disposed on a lateral side of a substrate and configured to emit a light beam to the lateral side for correspondingly penetrating the substrate. The method also provides an image capturing module for retrieving an image of the upper surface, wherein an incident angle of the light beam to the respective lateral side is limited within a first predetermined angle to allow the light beam to have a total reflection in the substrate. Thus, the light beam is blocked by internal defects when transmitting within the substrate to generate bright spots to be detected by the image capturing module for locating the defect position. The method provides a better image definition of internal defects images. The present invention further provides an apparatus based on the method for inspecting substrate internal defects.

6 Claims, 7 Drawing Sheets

APPARATUS AND METHOD FOR INSPECTING SUBSTRATE INTERNAL DEFECTS

BACKGROUND OF THE INVENTION

1. Field of the Invention

The invention generally relates to an apparatus and a method for inspecting substrate internal defects.

2. Description of Prior Art

Semiconductor manufacturing processes such as thin film deposition are used for fabricating electronic components on a substrate. Accordingly, the quantity of internal defects in the substrate such as inclusions, bubbles, cracks is a critical factor indicating the quality of electronic components. In addition, cracks crack are generated on substrates because substrates undergo processes such as high temperature heating process and etching and are transported frequently in manufacturing processes.

Thus, inspecting internal defects on a substrate is an indispensable non destructive inspection. At present, the most frequently used crack inspection method arranges illuminating light sources beneath the substrate to emit light beam towards the lower surface of the substrate and penetrate the substrate, and uses a camera to obtain an image of the upper surface of the substrate above the substrate. The penetration rate of the light beam is reduced as the emitted light beam is reflected, refracted and scattered by internal defects. The image brightness of locations having internal defects is significantly lowered than other areas so that the locations and sizes of the internal defects can be identified by image analysis of human or computing devices subsequently.

Figure 1:
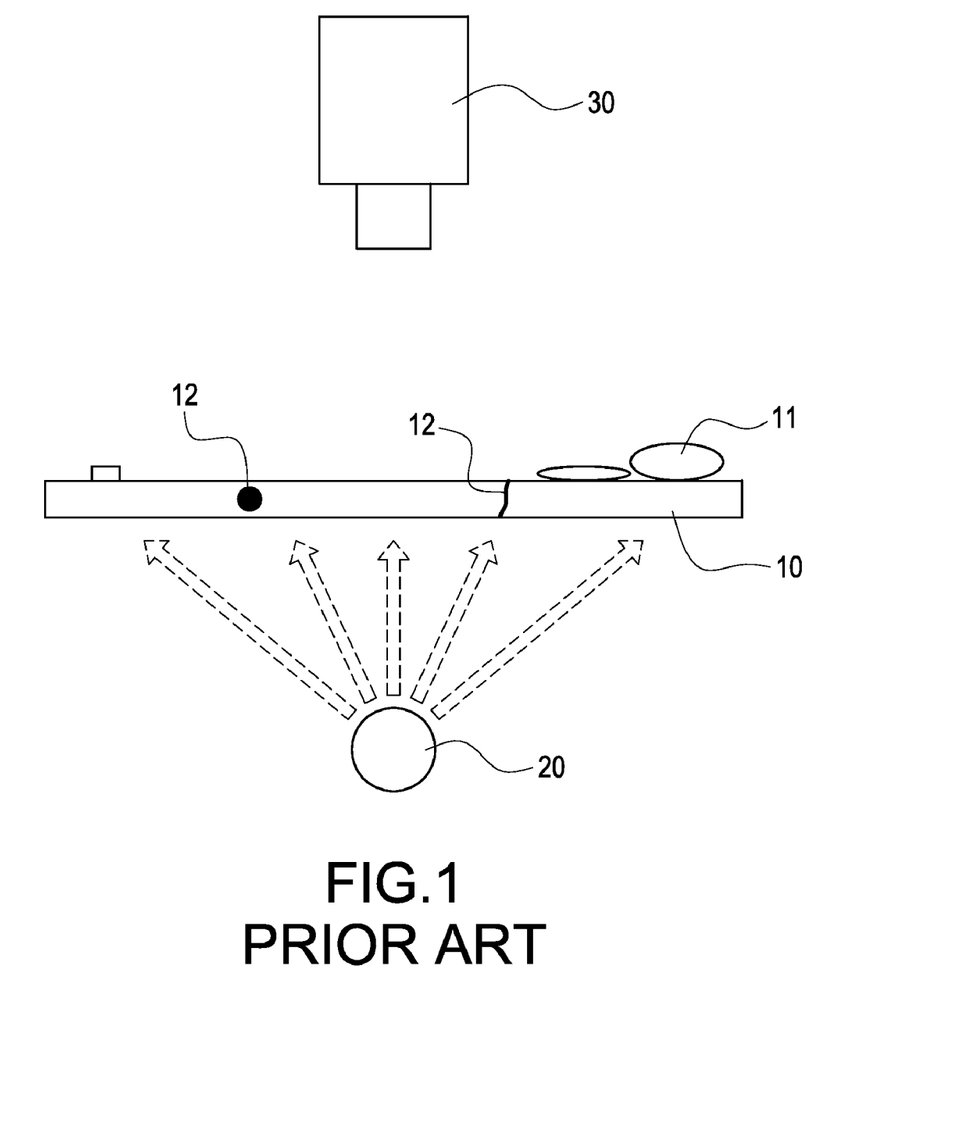
FIG. 1 is a schematic diagram of an prior art apparatus for inspecting substrate internal defects.

The image definition of internal defects images determines the effectiveness of the inspection and efficiency of image analysis. Therefore, acquiring precise and clear images of internal defects has been an eager need to resolve in the inspection processes. Nonetheless, the above internal defects inspection has the following disadvantages. Firstly, as shown in the schematic diagram illustrating the above method for inspecting internal defects in FIG. 1, not only surface pollutants 11 adhered on two sides of a substrate 10 or the texture of the substrate 10 but also internal defects 12 such as inclusions or cracks would influence penetration rate of light beam during the manufacturing process. It is not effective to differentiate between internal defects 12 and surface pollutants 11 according to dark spots when interpreting images retrieved by a camera 30. Frequently, surface pollutants 11 are misinterpreted as internal defects 12.

Figure 2:
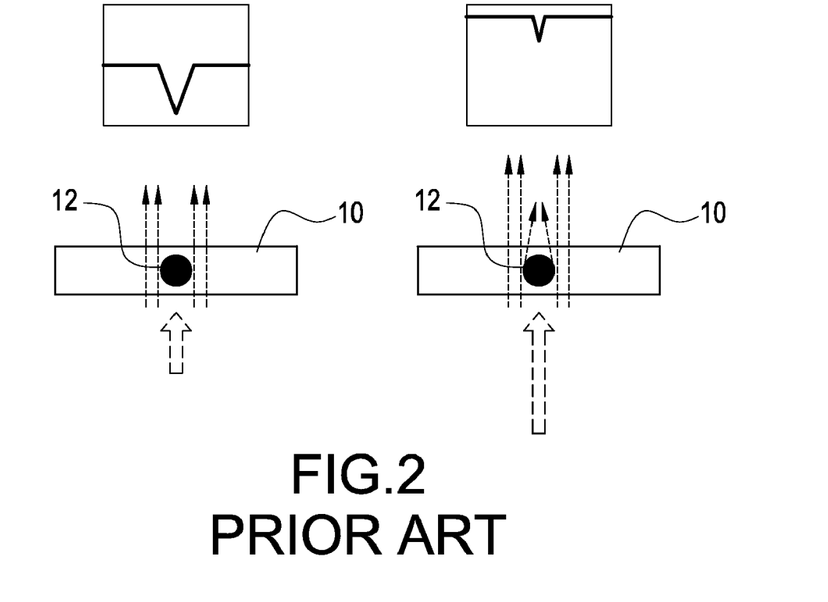
FIG. 2 is a schematic diagram illustrating the apparatus for inspecting substrate internal defects performing a substrate inspection.
Figure 3:
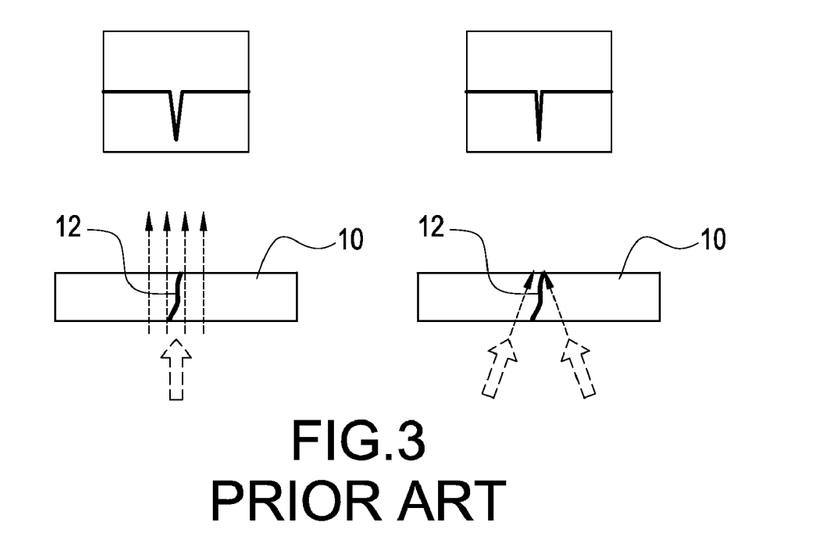
FIG. 3 is another schematic diagram illustrating the apparatus for inspecting substrate internal defects performing a substrate inspection.

As shown in FIG. 2, light beam diffracts as the light beam is interfered such that micro internal defects 12 in an image may be faded when emitting brightness of light beam become stronger. In other words, the image width of internal defects 12 is in inverse proportion to the light intensity. There are circumstances emitting light intensity is increased on a thicker substrate 10 in order to increase image brightness. Yet, when light intensity is higher than a certain level, light intensity of diffraction generated then becomes too strong which lowers the image definition of internal defects 12. Thus, it is required to spend higher cost on a camera with higher definition to retrieve clear image. In addition, under the circumstance when the tolerance of a substrate 10 is large, an optimal light intensity for retrieving the best image becomes a difficult decision. Further, as shown in FIG. 3, when crack width of micro defects 12 under non parallel light becomes smaller, it is difficult to enhance image definition of micro crack by projecting light from different directions. Photo of the attachment 1 is a photo of crack image taken by prior art method for inspecting defects.

SUMMARY OF THE INVENTION

As a result, the present invention provides an illuminating method special designed for substrate inspection to resolve the above problems. The present invention uses the total reflection of light beam within a substrate to directly illuminate internal defects in the substrate so as to enhance the image definition of internal defects such as cracks, pores, impurities, bubbles, thickness difference and effectively avoid misidentifying foreign objects such as surface stains as internal defects. In addition to offering a more efficient capability to inspect internal defect, the method also can resolve the difficulty to inspect substrate internal defects after the substrate finished surface mount process.

Therefore, it is the objective of the present invention to provide a method for inspecting substrate internal defects for receiving higher image definition of internal defects in a substrate.

In order to achieve the above objective, the present invention provides the method for inspecting substrate internal defects, the substrate has an upper surface and a plurality of lateral sides connected to the upper surface. The method for inspecting substrate internal defects firstly provides at least one light source disposed on one of the lateral sides on the substrate and configured to emit a light beam to the lateral side for correspondingly penetrating the substrate. The method also provides an image capturing module disposed above the substrate for retrieving an image of the upper surface, wherein an incident angle of the light beam to the respective lateral side is limited within a first predetermined angle to allow the light beam to have a total reflection in the substrate.

Further, it is another objective of the present invention to provide an apparatus for inspecting substrate internal defects for receiving higher image definition of internal defects in a substrate.

The present invention provides the apparatus for inspecting substrate internal defects, wherein the substrate has an upper surface and a plurality of lateral sides connected to the upper surface. The apparatus for inspecting substrate internal defects has at least one light source and an image capturing module. The light source is disposed on one of the lateral sides on the substrate and configured to emit a light beam to the lateral side for correspondingly penetrating the substrate. The image capturing module is disposed above the substrate for retrieving an image of the upper surface, wherein an incident angle of the light beam to the respective lateral side is limited within a first predetermined angle to allow the light beam to have total reflection in the substrate.

The present invention renders light beam transmitting into a substrate and has a total reflection within the substrate where the light beam does not refract out of the substrate. When light beam is interfered by internal defects within the substrate, light beam moving path is changed. Such changes of light moving path result in reflection, refraction or scattering, and generate bright spots. Thus, the defect locations are detected by an image capturing module above the substrate. The method is effective in improving image definition of internal defects and offering higher detectability on internal defects

BRIEF DESCRIPTION OF DRAWING

The features of the invention believed to be novel are set forth with particularity in the appended claims. The invention itself, however, may be best understood by reference to the following detailed description of the invention, which describes an exemplary embodiment of the invention, taken in conjunction with the accompanying drawings, in which:

DETAILED DESCRIPTION OF THE INVENTION

In cooperation with attached drawings, the technical contents and detailed description of the present invention are described thereinafter according to a preferable embodiment, being not used to limit its executing scope. Any equivalent variation and modification made according to appended claims is all covered by the claims claimed by the present invention.

Figure 4:
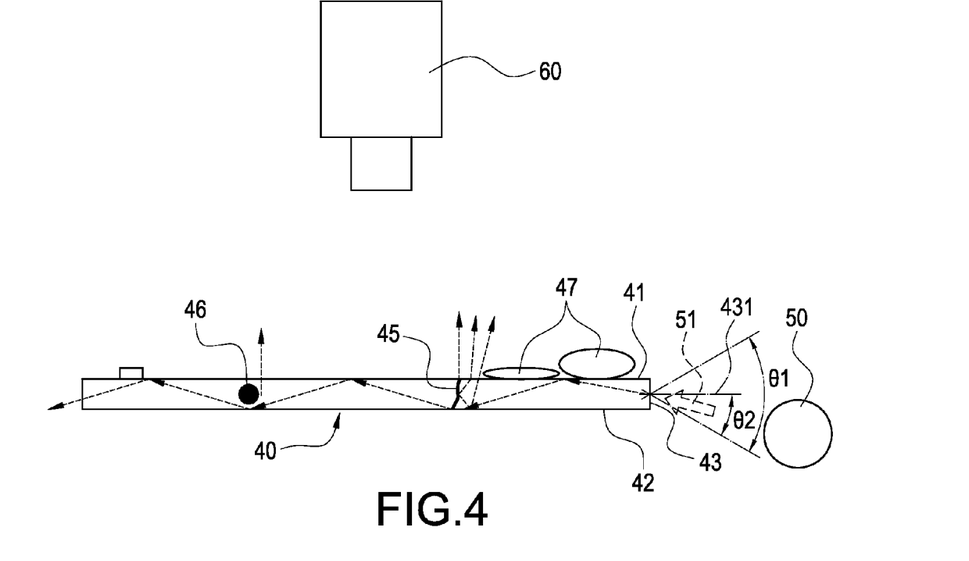
FIG. 4 is a schematic diagram of an apparatus for inspecting substrate internal defects according to the present invention.

FIG. 4 is a schematic diagram of a preferred embodiment according to the present invention. The apparatus for inspecting substrate internal defects is suitable for use in internal defects inspection of a substrate 40. The apparatus for inspecting substrate internal defects mainly comprises a light source 50, and an image capturing module 60.

The light source 50 is disposed on one of the lateral sides 43 of the substrate 40 to emit a light beam 51 to the lateral side 43 for correspondingly penetrating the substrate 40. Preferably, the light beam emitted by the light source 50 moves along the same path to have stronger light beam transmitting in the substrate 40. In the embodiment, the substrate 40 is a silicon wafer, the light source 50 selected is an infrared light source which is capable of penetrating the silicon wafer accordingly. In other embodiments, alternatives of the light source 50 are not limited to the above embodiment. For example, if the substrate 40 is made of glass, visible light source is applicable as the light source 50.

Figure 5:
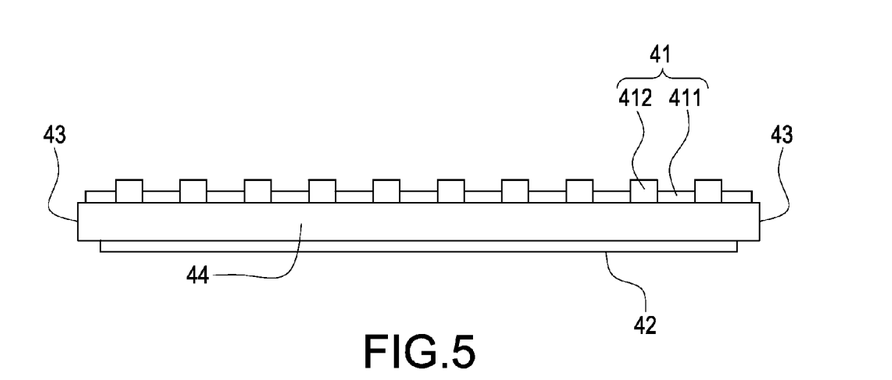
FIG. 5 is a schematic diagram of an apparatus for inspecting substrate internal defects according to the present invention.

Substantially, as shown in FIG. 5, the substrate 40 of the embodiment is a solar cell substrate, but is not limited to the above in other embodiments. The substrate 40 has a main body 44, an upper surface 41 and a lower surface 42, and a plurality of lateral sides 43 connecting the upper surface 41 and the lower surface 42. The upper surface 41 comprises a plurality of anti reflection portion 411 and metal electrode portion 412 which are staggered, wherein the anti reflection portion 411 is light transmissive and the metal electrode portion 412 is light tight. The lower surface 42 is a light tight metal conducting portion. The plurality of lateral sides 43 is largely perpendicular to the upper surface 41 and the lower surface 42.

It should be noted that, as shown in the FIG. 4, the incident angle of the light beam 51 emitted by the light source 50 to the respective lateral side 43 is limited by a first predetermined angle θ1 in order to effectively differentiate substrate internal defects and external defects in the present invention and assure the incident light beam 51 in substrate 40 has a total reflection. The first predetermined angle θ1 is determined according to wavelength of the light beam 51 and refraction index of the substrate 40 and can be obtained by prior art optical formulas.

In addition to limiting the incident angle of the light beam 51 within first predetermined angle θ1, because applied thickness of the substrate 40 is mostly smaller than 1 mm and the position of the substrate 40 relative to the position of the light source 50 may offset slightly, the diameter of the light source 50 is usually larger than the thickness of the substrate 40 such that emitted light beam by the light source 50 is allowed to transmit into the substrate 40. Consequently, part of the light beam transmitting onto the upper surface 41 of the substrate 40 may scatter and become a part of the image taken by the image capturing module 60. In order to avoid the scattering light effecting on the contrast ratio of the image retrieved by the image capturing module 60, the incident angle of the light beam 51 according to the present invention is further limited to the respective lateral side 43 within a second predetermined angle θ2. The second predetermined angle θ2 is a far half the first predetermined angle θ1 away from the image capturing module. The emitted light beam 51 transmits to the substrate 40 by the second predetermined angle θ2 instead of directly illuminating on the upper surface 41, and transmits in the substrate 40 to have a total reflection within the upper surface 41 or the lower surface 42 of the substrate 40 instead of refracting outside of the substrate 40.

The image capturing module 60 is disposed above or beneath the substrate 40 for retrieving images of the upper surface 41 of the substrate 40. In the embodiment, the upper surface 41 of the substrate 40 comprises the light transmissive anti reflection portion 411 and the light tight metal electrode portion 412 and the lower surface 42 is a light tight metal conducting portion. As a result, the image capturing module 60 is disposed above the substrate 40 for detecting reflection, refraction and scattering of the light beam 51 generated by internal defects such as crack 45 and inclusion 46 via the anti reflection portion 412 of the upper surface 41. The image capturing module 60 is not limited to some specific models and can be any types of image detectors such as cameras and recorders.

Generally speaking, when the light beam 51 illuminates on the lateral side 43 of the substrate 40 with incident angle within the second predetermined angle θ2, the light beam 51 transmits successfully in the substrate 40. If not, when incident angle of the light beam 51 falls out of the second predetermined angle θ2, only small part of the light beam transmits in substrate 40 whilst most of the light beam penetrates the substrate 40 and generates a bright area, which may cause confusion when interpreting the image data. Also, the ratio of the light beam transmitting in the substrate 40 is lower as the light beam 51 has larger offset from the second predetermined angle θ2.

Following the light beam 51 transmitting in the substrate 40, the majority of the light beam 51 has a total reflection within substrate 40. Provided there is no defect in the materials of substrate 40, then the light beam 51 does not refract out of the substrate 40 and may continue to move until the energy exhausted or transmit out of the substrate 40 from the other side of the lateral sides 43. The light beam 51 can be interfered by the material interface such as cracks 45 or internal defects resulting from material difference such as inclusions 46, bubbles, internal impurities when the light beam 51 transmits within the substrate 40. Under the circumstance, the moving path of the light beam 51 changes and light beam moving path is changed. Such changes of light moving path result in reflection, refraction or scattering transmitting outside of upper surface 41 of the substrate 40 to generate bright spots. Thus, the defect locations are detected via image capturing module 60 above the substrate 40. The photo of the attachment 2 is a crack photo taken according to the present invention. Compared to the photo of attachment 1 using prior art defect inspecting method, the crack image of the present invention is substantially more detailed.

However, foreign objects 47 on the upper surface 41 of the substrate 40 almost have no effect on internal moving path of the light beam 51 within the substrate 40. For example, foreign objects 47 on the upper surface 41 may include dusts, plastic particles, oil stains, water marks and finger prints. Because light beam 51 from the substrate 40 does not penetrate foreign objects 47, the photo retrieved by the image capturing module 60 does not include the light beam 51 penetrating the location of the foreign objects 47. Therefore, the foreign objects 47 are not misidentified as the internal defects of the substrate 40 in the image analysis. Further, transmitted light beam through the micro surface texture on the upper surface 41 of the substrate 40 caused by etching is small that is not detectable by the image capturing module 60 so that it is identified with the internal defects of the substrate 40 image capturing module.

Figure 6:
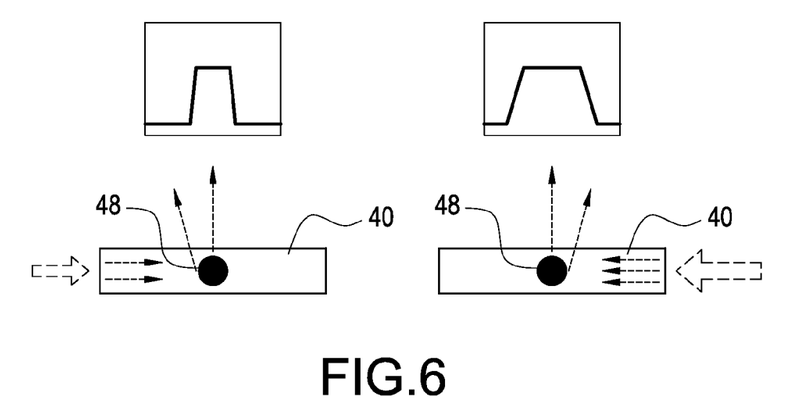
FIG. 6 is a schematic diagram of an apparatus for inspecting substrate internal defects according to the present invention.
Figure 7:
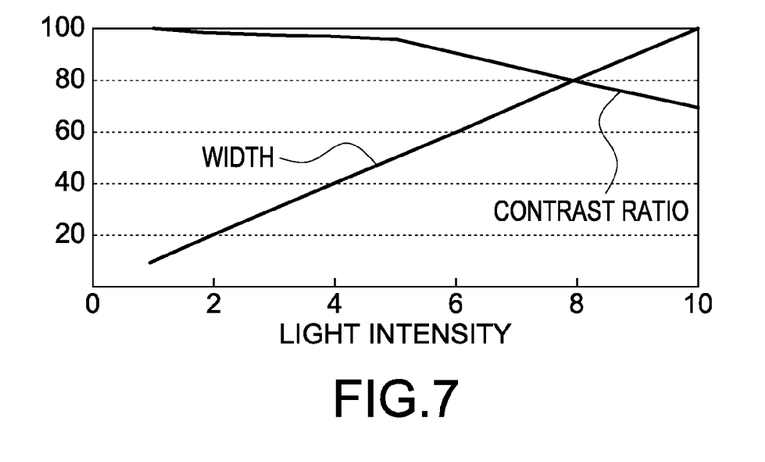
FIG. 7 is a curve diagram of light intensity to relative image signal width and to relative image signal contrast ratio.

FIG. 6 illustrates the method used by the present invention is effective in improving image definition by increasing light intensity to form signals of bright spots based on interface scattering principles. The left part of the photo was taken with lower light intensity. In contrast, the right part of the photo is taken with higher light intensity. The higher light intensity generates image signals of wider width of internal defects so that the higher light intensity can be used for detecting extreme small cracks on material interfaces. FIG. 7 is a curve diagram of light intensity to relative image signal width and to relative image signal contrast ratio. In FIG. 7, when the light intensity increases, the image signal width of cracks increases and overall contrast ratio decreases slightly which is beneficial to image interpretation.

Figure 8:
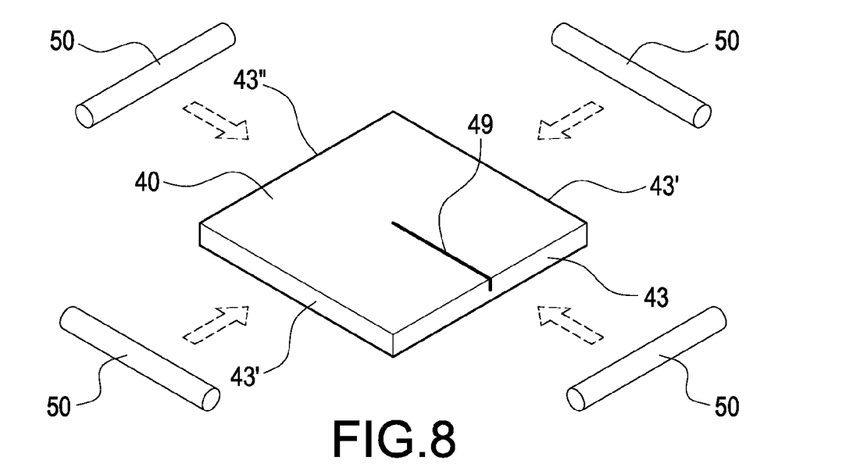
FIG. 8 is a schematic diagram of an apparatus for inspecting substrate internal defects according to the present invention.

FIG. 8 is a schematic diagram of an apparatus for inspecting substrate internal defects according to the present invention. The embodiment further provide a plurality of light sources 50 to emit light beam from multiple lateral sides 43, 43', 43" of the substrate 40 for penetrating the substrate 40 in order to further increase image brightness and width of internal defects 49 in the substrate 40. The plurality of light sources 50 can be linear light source and parallel to the direction along the plurality of lateral side 43, 43', and 43". The internal defects 49 may be directional as shown in the diagram. Under the circumstance, the extending direction of the internal defects 49 is largely perpendicular to the lateral side 43, the image brightness of the internal defects generated by light beam from lateral side 43 is much lower than the image brightness of the internal defects generated by light beam from lateral side 43'. As shown in the FIG. 9, the image signal width of the internal defects is effectively improved when light beam transmits from multiple directions along the direction largely perpendicular to the extending direction of the internal defects 49.

Figure 9:
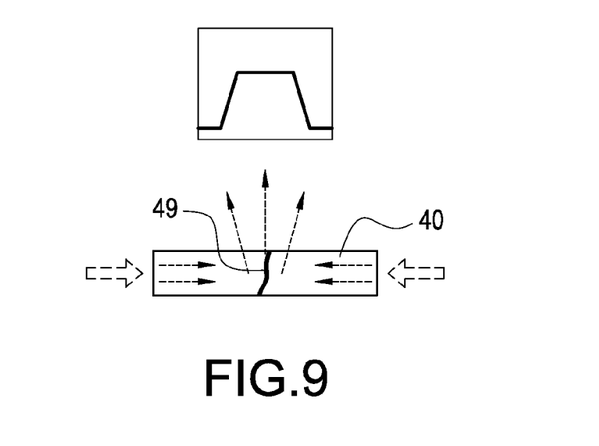
FIG. 9 is a schematic diagram of an apparatus for inspecting substrate internal defects according to the present invention.

The problem that the amount of transmitted light beam is small caused by directionality of the internal defects 49 can be resolved by increasing brightness of the internal defects 49 via transmit light beam from the lateral side 43, 43', 43" of the substrate 40. Since the image light intensity is superimposed by light beam from multiple directions, image recognition rate on micro cracks can be effectively improved, and required maximum resolution of the image capturing module 60 can be lowered significantly which offers advantages of lowering production cost and providing more alternatives when choosing image capturing modules.

Figure 10:
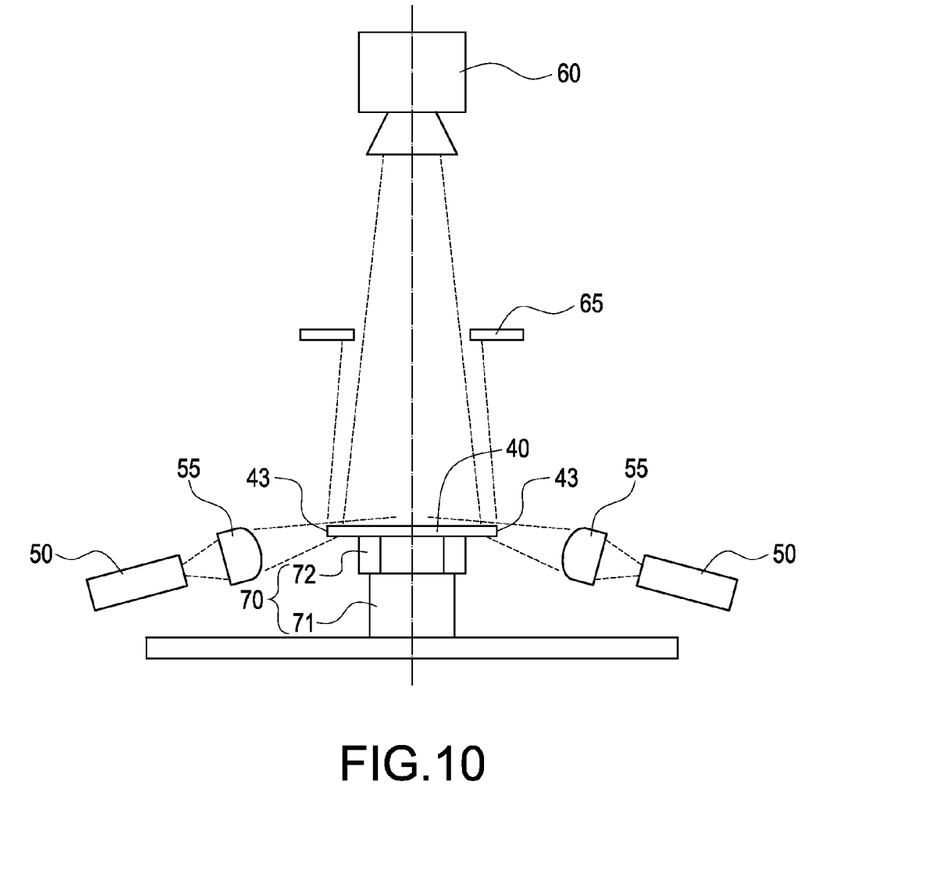
FIG. 10 is a schematic diagram of an apparatus for inspecting substrate internal defects according to the present invention.
Figure 11:
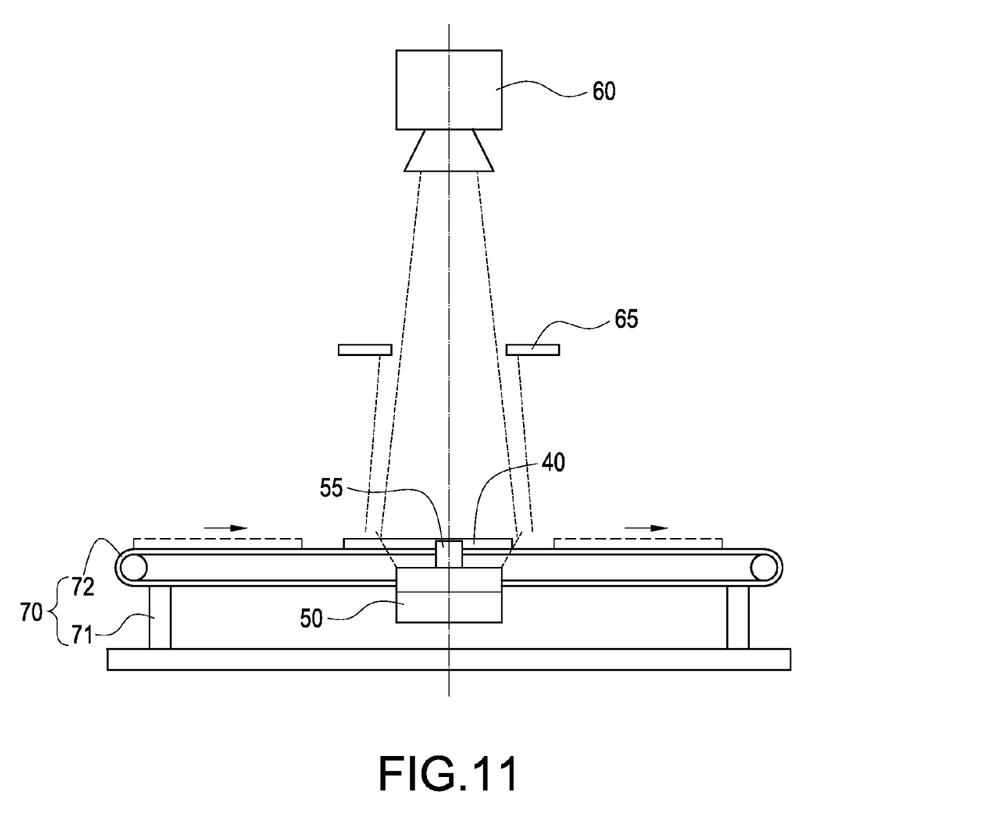
FIG. 11 is a schematic diagram from the other lateral side of an apparatus for inspecting substrate internal defects according to apparatus in FIG. 10.

FIG. 10 and FIG. 11 are other embodiments of the present invention. Compared with the above embodiment, the embodiment further comprises a carrier 70 for carrying the substrate 40, the carrier 70 comprises a base 71 and a transmission module 72 disposed on the base 71. The transmission module 72 drives the substrate 40 to move along a horizontal direction relative to the image capturing module 60 (as the arrow direction shown in the FIG. 11). In addition, the light source 50 emits light beam towards the lateral side 43 of the substrate 40 via a condensing lens 55 to have the light beam focus on the lateral side 43. In other words, the light beam emitted by the light source 50 illuminates only on part of the lateral side 43 instead of illuminating on whole lateral side 43. Further, the embodiment further uses a shading plate 65 with an opening between the photo taking device 60 and the substrate 40. The shading plate 65 is used for reducing the effect of external light beam on the photo taking device 60 such that the photo taking device 60 may precisely retrieve image of the upper surface 41 of the substrate 40 through the opening on the shading plate 65.

When the substrate 40 is driven by the transmission module 72 and moves along the horizontal direction relative to the photo taking device 60, the light beam 51 emitted by the light source 50 scans horizontally on the lateral side 43 of the substrate 40 and the photo taking device 60 take photos on the upper surface 41 of the substrate 40 continuously. As such, the transmission module 72 continuously performs inspection on the substrate 40. Also, the apparatus according to the embodiment can be integrated with on line manufacturing process facilities to configure inspections pre process, in process and post process.

As the skilled person will appreciate, various changes and modifications can be made to the described embodiments. It is intended to include all such variations, modifications and equivalents which fall within the scope of the invention, as defined in the accompanying claims.

What is claimed is:
1. A method for inspecting substrate internal defects, comprising:
   providing a solar cell substrate having an upper surface, a lower surface and a plurality of lateral sides connected between the upper surface and the lower surface;
   providing at least one light source disposed on one of the lateral sides on the substrate and configured to emit a light beam to the lateral side for correspondingly penetrating the substrate; and
   providing an image capturing module disposed above the substrate for retrieving an image of the upper surface;

wherein an incident angle of the light beam to the respective lateral side is limited within a first predetermined angle, and the first predetermined angle is a critical angle to allow the light beam to have total reflection in the substrate and is defined by an included angle between a light ray propagation direction and a normal line to the lateral surface;

wherein the incident angle of the light beam to the respective lateral side is limited within a second predetermined angle, the second predetermined angle is the far half of the first predetermined angle away from the image capturing module;

wherein a center of the light source is located substantially at an angle-bisecting line of the second predetermined angle;

wherein a width of the lateral side is defined by a thickness of the substrate, and a diameter of the light source is larger than the width of the lateral side; and wherein the light beam emits the light beam towards the lateral side of the substrate via a condensing lens to have the light beam focus on the lateral side so that the light beam emitted by the light source illuminates only on part of the lateral side instead of illuminating on whole lateral side.

2. The method for inspecting substrate internal defects of claim 1, wherein the method comprises a plurality of light sources emitting light beam to the plurality of lateral side respectively for penetrating the substrate.

3. An apparatus for inspecting substrate internal defects, comprising:
- a solar cell substrate having an upper surface, a lower surface and a plurality of lateral sides connected between the upper surface and the lower surface;
- at least one light source disposed on one of the lateral sides of the substrate and configured to emit a light beam to the lateral side for correspondingly penetrating the substrate; and
- an image capturing module disposed above the substrate for retrieving an image of the upper surface;

wherein an incident angle of the light beam to the respective lateral side is limited within a first predetermined angle, and the first predetermined angle is a critical angle to allow the light beam to have total reflection in the substrate and is defined by an included angle between a light ray propagation direction and a normal line to the lateral surface;

wherein the incident angle of the light beam to the respective lateral side is limited within a second predetermined angle, the second predetermined angle is the far half of the first predetermined angle away from the image capturing module;

wherein a center of the light source is located substantially at an angle-bisecting line of the second predetermined angle;

wherein a width of the lateral side is defined by a thickness of the substrate, and a diameter of the light source is larger than the width of the lateral side; and wherein the light beam emits the light beam towards the lateral side of the substrate via a condensing lens to have the light beam focus on the lateral side so that the light beam emitted by the light source illuminates only on part of the lateral side instead of illuminating on whole lateral side.

4. The apparatus for inspecting substrate internal defects of claim 3, wherein the apparatus comprises a plurality of light sources emitting light beam to the plurality of lateral side respectively for penetrating the substrate.

5. The apparatus for inspecting substrate internal defects of claim 3, wherein the plurality of light sources are linear light source and parallel to the plurality of lateral sides respectively.

6. The apparatus for inspecting substrate internal defects of claim 3, further comprising a carrier for carrying the substrate, the carrier comprising a base and a transmission module disposed on the base, the transmission module driving the substrate to move along a horizontal direction relative to the image capturing module.

* * * * *